United States Patent
Leung et al.

(10) Patent No.: US 6,774,254 B2
(45) Date of Patent: Aug. 10, 2004

(54) GOLD COMPLEXES

(75) Inventors: Pak Hing Leung, Singapore (SG); Soh Ha Chan, Singapore (SG); Yongcheng Song, Kanagawa (JP)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 10/240,119

(22) PCT Filed: Apr. 9, 2001

(86) PCT No.: PCT/SG01/00060

§ 371 (c)(1),
(2), (4) Date: Sep. 26, 2002

(87) PCT Pub. No.: WO01/77121

PCT Pub. Date: Oct. 18, 2001

(65) Prior Publication Data

US 2003/0114695 A1 Jun. 19, 2003

Related U.S. Application Data

(63) Continuation-in-part of application No. 09/588,690, filed on Jun. 7, 2000, now abandoned.

(30) Foreign Application Priority Data

Apr. 10, 2000 (SG) ..................... 200001699-8

(51) Int. Cl.$^7$ ............................ C07F 1/12; A61K 31/28
(52) U.S. Cl. ............................ 556/23; 556/20; 556/21; 514/495
(58) Field of Search ............................ 556/20, 21, 23; 514/495

(56) References Cited

U.S. PATENT DOCUMENTS 4,766,226 A    8/1988  Hill et al. ..................... 556/18

FOREIGN PATENT DOCUMENTS

EP    0151046    8/1985

*Primary Examiner*—Porfirio Nazario-Gonzalez
(74) *Attorney, Agent, or Firm*—Klarquist Sparkman, LLP

(57) ABSTRACT

Novel phosphino-gold (I) compounds, a process for their preparation, pharmaceutical compositions containing such phosphino-gold (I) compounds and their use in the treatment of cancer disease are disclosed.

151 Claims, 1 Drawing Sheet

GOLD COMPLEXES

RELATED APPLICATION

This is the National Stage of International Application No. PCT/SG01/00060, filed Apr. 9, 2001, which is a continuation-in-part of application Ser. No. 09/588,690, filed Jun. 7, 2000, now abandoned.

FIELD OF THE INVENTION

The present invention relates to novel phosphino-gold(I) compounds, to a process for preparing same and to the use of such phosphino-gold(I) compounds for the treatment of cancer.

BACKGROUND OF THE INVENTION

To date, in the prior art there are only a limited number of efficient anti-cancer drugs available to treat the wide spectrum of cancerous diseases. Amongst the few licensed drugs, cisplatin and its carboplatin derivative (platinum based) are considered to be the most powerful and efficient drugs. These drugs are currently being used almost universally in the treatment of testicular, ovarian and several other forms of cancer. Unfortunately, these drugs also induce major side effects like template inactivation of DNA, destroying rapidly dividing normal body cells and causing serious damage to the bone marrow.

It was discovered In the mid 80s that phosphine-supported gold(I) complexes showed significant anti-tumor activities. Since phosphines are not natural products and are generally difficult to prepare, clinical tests thus far of such anti-cancer gold drugs have been limited to some simple and non-designed phosphines that are available commercially. This has led to irregular and uncontrolled test results.

It would be a significant advance in the art if a new class of anti-cancer drugs could be developed which are effective, and induce minimum side effects.

It is accordingly an object of the present invention to overcome, or at least alleviate, one or more of the difficulties or deficiencies related to the prior art.

SUMMARY OF THE INVENTION

Accordingly, in a first aspect of the present invention, there is provided a phosphino-gold(I) compound of formula (I):

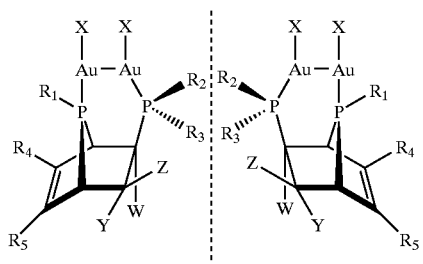

wherein $R_1$, $R_2$, $R_3$, $R_4$ and $R_5$, each of which may be the same or different, are selected from the group consisting of hydrogen, optionally substituted alkyl, aryl, alkenyl, alkynyl, hydroxyalkyl, alkoxy, aryloxy, carboxyalkyl, alkoxycarbonyl, hydroxy, alkylthio, alkylsulfinyl and alkylsulfonyl;

Z is hydrogen or a functional group;
Y is hydrogen or a functional group;
W is hydrogen or a functional group; and
X is a halogen or $C(F)_3$ or $C(Cl)_3$;
in an optically active or racemic form; or a salt thereof.

Alkyl groups preferably contain up to 10 carbon atoms, and more preferably 1 to 4 carbon atoms. The term "alkyl" includes both straight- and branched-chain alkyl groups and cycloalkyl groups. References to individual alkyl groups such as "propyl" are specific for the straight chain version only. An analogous convention applies to other generic terms.

The term "aryl" refers to compounds having one or more aromatic rings having 6 to 16 carbon atoms.

Except as provided otherwise, the terms "alkyl" and "aryl" have the same meaning however used, for example when used alone, or as prefix or suffix.

The term "alkenyl" refers to an alkyl as described above with at least one double bond, it being understood that an "alkenyl" will contain at least 2 carbon atoms.

The term "alkynyl" refers to an alkyl as described above with at least one triple bond, it being understood that an "alkynyl" will contain at least 2 carbon atoms.

By the term "optionally substituted", we mean that each group may carry one or more of the substituents selected from halo, nitro, cyano, hydroxy, amino, (1–4)C alkyl, (1–4)C alkoxy, and (1–4)C alkylamino.

By the term "halogen", we mean bromide, fluoride, iodide or chloride.

A suitable value for each of $R_1$, $R_2$, $R_3$, $R_4$, and $R_5$ when it is (1–4C)alkyl or for a (1–4C)alkyl substituent is, for example, methyl, ethyl, propyl, isopropyl, butyl or isobutyl.

A suitable value for each of $R_1$, $R_2$, $R_1$, $R_4$, and $R_5$ when it is (1–4C)alkoxy or for a (1–4C)alkoxy substituent is, for example, methoxy, ethoxy, propoxy, butoxy or isobutoxy.

A suitable value for $R_1$, $R_2$, $R_3$, $R_4$, and $R_5$ when it is (1–4C)alkylamino or for a (1–4C)alkylamino substituent is, for example, methylamino, ethylamino, propylamino, isopropylamino, butylamino or isobutylamino.

The functional groups in position Z, Y and W are selected based on their ability to enhance the hydrophilic property, acidity/alkalinity and to reduce toxicity. without adversely affecting the anti-tumor activity and may be selected from hydroalkyl, alkoxy, aryloxy, carboxyalkyl, alkoxycarbonyl, hydroxy, alkylthio, alkylsulfinyl and alkylsufonyl.

It will be understood that a phosphino-gold(I) compound of the present invention may possess one or more asymmetric carbon atoms and it can therefore exist in diastereoisomeric racemic and optically active forms. It will be understood that the invention encompasses any such form, it being a matter of common general knowledge how various diastereoisomeric forms may be separated and how a racemic compound may be separated into its optically-active forms.

It is also to be understood that the compounds of the present invention may exist in solvated as well as unsolvated forms such as, for example, hydrated forms. It is to be understood that the invention encompasses all such solvated forms.

It has surprisingly been found that the phosphino-gold(I) complexes according to the present invention exhibit significant anti-tumor activity but with reduced side effects relative to known anti-tumor agents such as cisplatin and its carboplatin derivatives.

The present invention therefore also relates to a use of a compound of formula (I) in an optically active or racemic form, or a pharmaceutically acceptable salt thereof, to produce an antiproliferative effect in an animal; and to treat cancer. The invention also relates to its use in the manufacture of a medicament for use in the production of an antiproliferative effect; and in the treatment of cancer.

The invention also relates to a process for producing antiproliferative effect, and to a process for treating cancer, comprising administering an effective amount of a compound of formula (I) in an optically active or racemic form or a pharmaceutically acceptable salt thereof. An effective amount refers to an amount effective, at dosages and for periods of time necessary to achieve the desired therapeutic result and may vary according to factors such as the disease state, age, sex and weight of the subject being treated.

In a further aspect of the present invention there is provided a pharmaceutical composition which includes an effective amount of a compound according to the invention and a pharmaceutically acceptable carrier or diluent. It will be understood that any salt of a compound of formula (I) selected for use in the composition is a pharmaceutically acceptable salt. This composition may be used to inhibit the growth and in some cases cause complete regression of tumor cells which are sensitive to the active ingredient which is the compound of formula (I).

The invention also provides a method of preparing a compound according to formula (I) in an optically active or racemic form, or a salt thereof, comprising reacting a compound of the formula shown below, wherein $R_1$, $R_2$, $R_3$, $R_4$ and $R_5$, Z, Y, and W are as described above, with a halo gold (I) compound to form a phosphino-gold (I) compound:

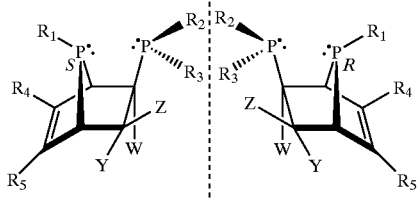

A suitable pharmaceutically-acceptable salt of an anti-tumor agent of the present invention is, for example, an acid-addition salt of an anti-tumor agent of the invention which is sufficiently basic, for example, an acid-addition salt with, for example, an inorganic or organic acid, for example hydrochloric, hydrobromic, sulphuric, phosphoric, trifluoroacetic, citric or maleic acid.

In addition a suitable pharmaceutically-acceptable salt of an anti-tumor agent of the present invention which is sufficiently acidic is an alkali metal salt for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

DETAILED DESCRIPTION OF THE INVENTION

Figure 1:
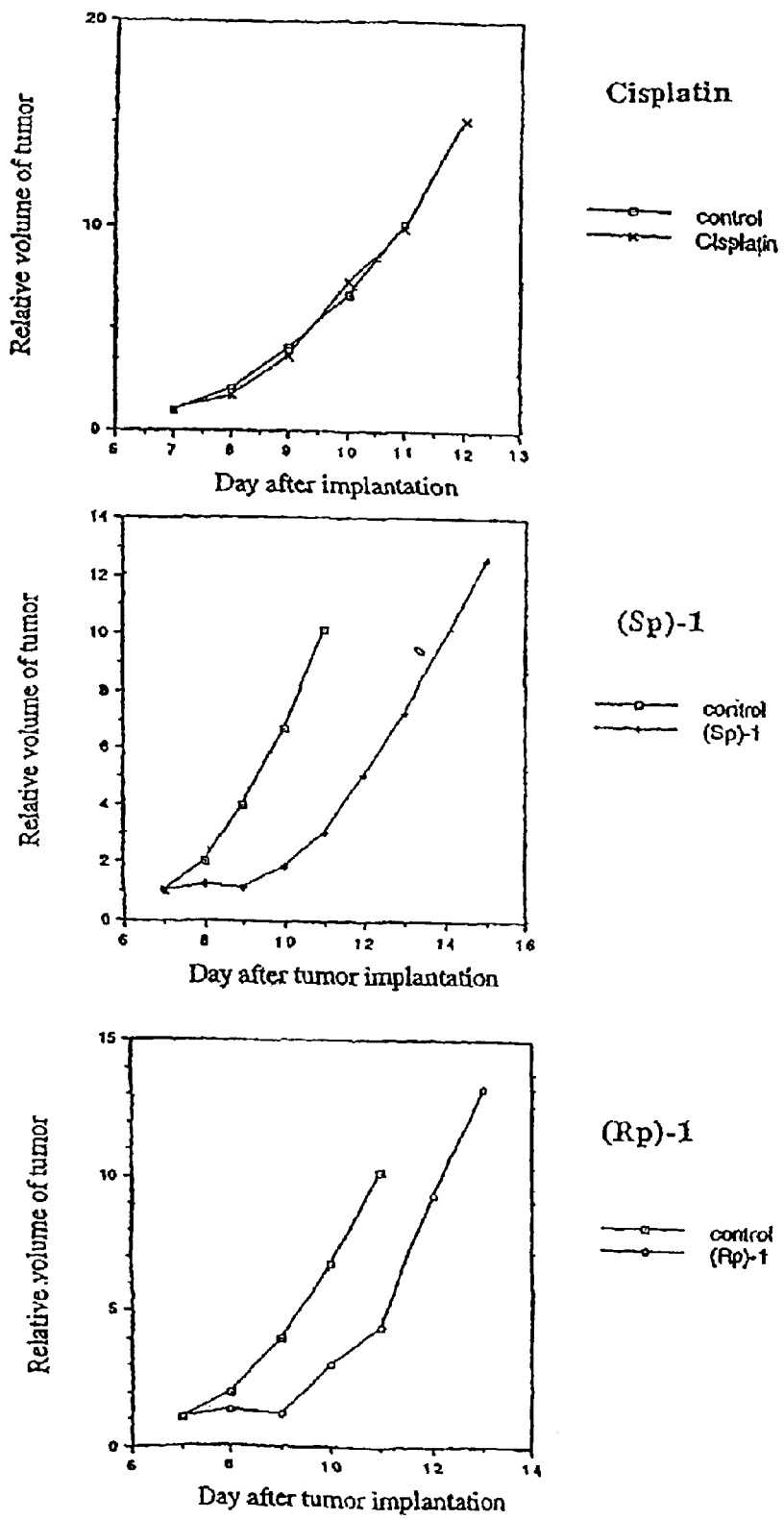
FIG. 1 shows the effect of cisplatin and compounds according to the invention, ((Sp)-1, and (Rp)-1) on the relative volume of tumor in mice. On Day 0, AKR mice were injected with K36 lymphoma cells. On Day 7, mice were divided into control and treatment groups. Treatment groups were injected intraperitoneally with either cisplatin, (Sp)-1, or (Rp)-1. Control groups were hot treated with any of the above compounds. On each subsequent day, the 3 treatment groups were injected with the respective compounds twice a day. Tumor weights were estimated from two-dimensional measurements on each day.

In a preferred form of the present invention, the phosphino-gold(I) compound may be of formula (II)

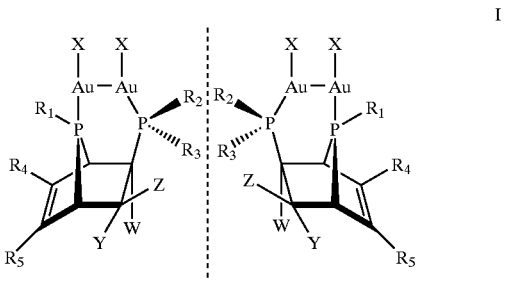

wherein
$R_1$=aryl or alkyl
$R_2$=aryl or alkyl
$R_3$=aryl or alkyl
$R_4$=aryl or alkyl
$R_5$=aryl or alkyl
Z=H or functional group
Y=H or functional group
W=H or functional group
X=halogen or $C(F)_3$ or $C(Cl)_3$ Preferably, alkyl groups contain up to 10 carbon atoms and more preferably 1 to 4 carbon atoms, and the functional group for Z, Y and W is selected from hydroalkyl, alkoxy, aryloxy, carboxyalkyl, alkoxycarbonyl, hydroxy, alkylthio, alkylsulfinyl and alkylsulfonyl.

A further preferred compound of formula (II) is a compound wherein $R_1$, $R_2$ and $R_3$ are phenyl $R_4$ and $R_5$ are methyl, Z and W are hydrogen and Y is ethoxycarbonyl ($CO_2Et$).

Preferred compounds of formula (I) include those in which each of $R_1$, $R_2$, $R_3$, $R_4$ and $R_5$ is independently hydrogen or an optionally substituted alkyl or aryl group. In one embodiment, $R_1$, $R_2$, $R_3$ are aryl and $R_4$ and $R_5$ are methyl.

Particularly preferred compounds of formula (I) include compounds in which each of $R_1$, $R_2$ and $R_3$ is independently an optionally substituted phenyl group and more preferably wherein each of $R_4$ and $R_5$ is independently hydrogen, methyl, ethyl, propyl or butyl, and more preferably, wherein Z and W are hydrogen and Y is an ethoxycarbonyl. The phenyl group may be substituted with (1–4C)alkoxy, and in one embodiment the substitutent is methoxy.

Still further preferred compounds of formula (I) include one of a pair of $S_p$- and $R_p$-enantiomers, wherein $R_1$, $R_2$ and $R_3$ are phenyl, $R_4$ and $R_5$ are methyl, X is chloro, Y is ethoxycarbonyl, Z and W are hydrogen, and $S_p$ or $F_p$ represents the absolute configuration at the bridgehead phosphorus atom of the phosphanorbomene skeleton. These compounds are preferred due to their distinct tumor-inhibiting activities in a variety of in vitro and in vivo test systems.

Specific preferred compounds according to the present invention may be selected from one or both of the following μ-{(1α,4α,5α(R),6β(S),7S)-5-(diphenylphosphino)-2,3-dimethyl-6-(ethoxycarbonyl)-7-phenyl-7-phosphabicyclo[2.2.1]hept-2-ene-P5,P7}bis[chlorogold(I)] ("($S_p$)-I")

μ-{(1α,4α,5α(S),6β(R),7R)-5-(diphenylphosphino)-2,3-dimethyl-6-(ethoxycarbonyl)-7-phenyl-7- phosphabicyclo[2.2.1]hept-2-ene-P5,P7}bis[chlorogold(I)] ("(R$_p$)-I")

The compounds of formula (I) according to the present invention may be produced by any suitable process. In an aspect of the present invention there is provided a process for the preparation of a phosphino-gold(I) compound of formula (I) as described above
in an optically active or racemic form; or a salt thereof;
which process includes reacting a compound of formula (III) with a halo gold (I) compound to form a phosphino-gold(I) compound

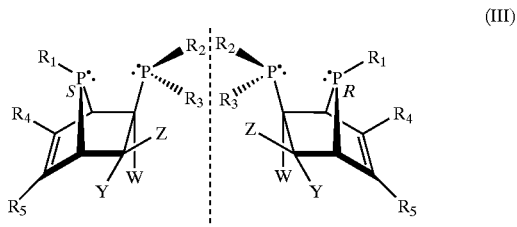

(III)

wherein R$_1$, R$_2$, R$_3$, R$_4$ and R$_5$, each of which may be the same or different, are selected from the group consisting of hydrogen, optionally substituted alkyl, aryl, alkenyl, alkynyl, hydroxyalkyl, alkoxy, aryloxy, carboxyalkyl, alkoxycarbonyl, hydroxy alkylthio, alkylsulfinyl and alkylsulfonyl;

Z is hydrogen or a functional group;

Y is hydrogen or a functional group; and

W is hydrogen or a functional group;

Preferably, alkyl groups contain up to 10 atoms, and more preferably 1 to 4 carbon atoms and the functional group for Z, Y and W are selected from hydroalkyl, alkoxy, aryloxy, carboxyalkyl, alkoxycarbonyl, hydroxy, alkylthio, alkylsulfinyl and alkylsufonyl.

In different embodiments of the process, R$_1$, R$_2$, R$_3$, R$_4$, R$_5$, Z, Y and W for formula (III) are selected to generate the preferred compounds of the invention described above. For example, (Sp) or (Rp)-ligand of formula (III) is reacted with a halogold(I) compound wherein R$_1$, R$_2$, and R$_3$ are phenyl, R$_4$, and R$_5$ are methyl, Y is ethoxycarbonyl and Z and W are hydrogen.

The process may be conducted in any suitable non-reactive solvent, for example a non-reactive organic solvent A solvent such as dichloromethane has been found to be suitable. Halogenated aliphatic or aromatic solvents, including chlorinated solvents, such as chloroform 1,2 dichloroethane and chlorobenzene may also be used. The amount of solvents used is dependant upon the amount of reactants used and on the solubility of reactants and varies from reagent to reagent. High concentration solutions are generally not recommended in chemical synthesis, and at least sufficient amounts of solvent must be used to dissolve the reactants.

The reaction may continue for a sufficient period of time to allow the compounds to fully react. The completion of the reaction may be confirmed in $^{31}$P NMR spectroscopy by reference to the phosphorus peaks of the resulting product which appear as two sets of doublets in the range of about 40–150 ppm. The process may be conducted, for example, at 0° C. to 100° C., preferably at ambient temperature, for a period of approximately 1 to 5 hours. At an ambient temperature of about 30°, the reaction may proceed for about 3 hours. Reaction time and temperature of the reaction mixture is dependant upon the phosphine ligand used and may vary with different ligands.

The halogold(I) compound may be of any suitable type, which will present the gold(I) ion in a suitably reactive manner. A chloro(dimethyl sulfide) gold(I) compound has been found to be suitable. Sodium tetrachloloaurate(III) .2H$_2$O gold(III) may also be reduced to gold(I) with excess thiodiglycol. The halogold(I) compound may be provided in a suitable solution, for example in the same solvent as is used for the formula (III) compound.

In a preferred aspect of the present invention, the preferred compounds may be prepared by reacting the appropriate (S$_p$)- or (R$_p$)-ligands of formula (III) with chloro(dimethyl sulfide)gold(I).

For example, a solution of the appropriate formula (III) compound in a non reactive organic solvent, such as dichloromethane, is reacted with a solution of chloro(dimethyl sulfide)gold(I) in the same solvent at ambient temperature for three hours to give the corresponding formula (I) compound.

The compounds of formula (III) may, for example, be prepared using the published method (Song, Y.; Mok K. F.; Leung, P.-H.; Chan, S.-H. *Inorg. Chem.*, 1998, 37, 6399.). Chloro(dimethyl sulfide)gold(I) is commercially available, for example, from Aldrich Chemical Company, Milawaukee, Mich., USA.

The compounds of formula (I), eg the preferred compounds, (S$_p$)-I and (R$_p$)-I exhibit tumor cell growth-inhibiting abilities. Accordingly, the compounds of the invention may be used to treat cancer, including tumorous cancer and to produce antiproliferative effect.

The cytotoxic and/or anti-tumor activities of the compounds of the present invention may be assessed using, for example one or more of the procedures set out below.

The human suspension tumor cell line assay determines the ability of a compound to inhibit the cells' ability to divide in vitro after a two hour exposure to the compound. The panel of human suspension tumor cell lines consist of Raji (B-cell lymphoma), Daudi (B-cell lymphoma), P3HR-1(B-cell lymphoma), and Molt-4 (T-cell leukemia). The cytotoxicity tests were carried out in vitro according to the following protocol:

Cryopreserved tumor cells were thawed and cultured in the media RPMI-1640 supplemented with 10% fetal calf serum (FCS) and 100 units/mL penicillin and 100 μg/mL streptomycin ("media R10"), in a 5% CO$_2$ humidified incubator at 37° C. They were subcultured every three days in a 75 cm$^2$ tissue culture flask.

A hemocytometer with four 1×1×0.1 mm$^3$ cells was used to count the cell concentration of a specified cell suspension solution. Trypan Blue was used to determine the viability of the counted cells, as live cells can exclude the dye penetration.

Each of Raji, Daudi, P3HR-1 and Molt-4 cells were dispensed into 6-well petri plates with 30,000 cells per well and were labelled in groups of three. A drug solution with a specified concentration was freshly prepared by dilution of a gold complex solution (1 mM) in DMSO with the media R10. Cell groups in triplicates were treated with the drug solution at three concentrations for 2 h at 37° C. in a CO$_2$ incubator, followed by aspiration of the drug solution. There was also a control with no drug treatment. Plates with tumor cells were washed once with 5 mL of phosphate-buffered saline (PBS) and fresh media R10 (5 mL) was added into each well of the petri plates. It should be noted that, since the cells are suspended in the media, they should be centrifuged down before removal of the media. Plates were then incubated at 37° C. in a CO$_2$ incubator for 5 days. The number of cells in each well was counted and the average value of triplicate samples were determined for each drug concentration. A least-square linear regression based on these data was carried out by Harvard Graphics (Version 3.0), and the $IC_{50}$ value (drug concentration at which cloning ability of tumor cells is inhibited by 50%) for the gold(I) complex was determined.

Table 1 lists the cytotoxicities ($IC_{50}$ in $\mu$M) of (Sp)- and (Rp)-1 against a variety of human suspension cell lines.

TABLE 1

| Compound | Daudi | Molt-4 | P3HR-1 | Raji |
| --- | --- | --- | --- | --- |
| $(S_p)$-I | 0.8 | 1 | 0.5 | 0.5 |
| $(R_p)$-I | 0.5 | 1 | 0.2 | 0.3 |

In addition, cytotoxicities of $(S_p)$-1 and $(R_p)$-1 against a human adherent tumor cell line, Mahlavu (liver cancer), were also evaluated according to the following protocol:

Cryopreserved Mahlavu cells were thawed and cultured as a monolayer in the media M10 (Dulbecco's modified eagle's medium supplemented with 10% FCS and 100 units/mL penicillin and 100 $\mu$g/mL streptomycin) in a 75 cm$^2$ tissue culture flask. The flask was kept in a 5% $CO_2$ humidified incubator at 37° C. Since the cells attached strongly to the bottom of culture flask, trypsin solution in PBS was used to detach the cells and then the Mahlavu cells were washed and counted as suspension cells.

10,000 cells were placed into each well of 6-well petri plates and incubated overnight to allow attachment to the plate. Triplicate samples of cells were allowed to react with the gold(I) complexes at three concentrations for four hours, followed by removal of the media. As before, a control with no drug treatment was included. The plates were then washed once with PBS(5 mL) and fresh media M10 (3 mL) was added. The plates were incubated at 37° C. in a $CO_2$ incubator for 5 days. The Mahlavu cells In each well were trypsinized and counted as usual.

The $IC_{50}$ values of $(S_p)$-I and $(R_p)$-I against this adherent tumor cell line were 6 and 8 $\mu$M, respectively. The $IC_{50}$ values were determined as described above.

Furthermore, cytotoxicities of $(S_p)$-1 and $(R_p)$-1 against normal lymphocytes from healthy adults were also assessed following the protocol described below 10 mL of fresh blood from healthy people was carefully lay red over 5 mL of Ficoll (a nonionic synthetic polymer of sucrose) in a sterile centrifuge tube. The tube was allowed to spin at a speed of 2,500 rpm. for 20 minutes. Following centrifugation, the blood mixture was separated to 4 layers according to their densities, i.e., from the top to the bottom, a layer of plasma, a layer of white blood cells, a layer of Ficoll, and a layer of red blood cells. The clear and pale yellow plasma layer was removed and the thin and opaque white blood cell layer was carefully transferred into a 75 cm$_2$ tissue culture flask containing the media R10 (15 mL). The flask was incubated at 37° C. overnight and then all of the floating lymphocytes (most of the other white blood cells attached to bottom of the flask) were carefully transferred into a test tube. Lymphocytes were washed and counted as suspension cells.

The procedure of the drug treatment of lymphocytes was similar to that of suspension tumor cells except that the lymphocytes were distributed into 5well plates with 100,000 cells/well. After the drug treatment, the cells were only incubated for 2 days before they were counted. The cytotoxicity test against normal lymphocytes revealed that the $IC_{50}$ value (determined as described above) of both (Sp)-1 and $(R_p)$-1 are much greater than 10 $\mu$M.

The compounds according to the present invention significantly inhibit tumor cell growth at concentration of a few micro molar scale. However, at those concentrations, they do not show toxic effects to the normal lymphocytes.

The in vivo anti-tumor activities of the phosphino-gold(I) compounds were evaluated using a murine tumor model, K36 lymphoma (T-cell lymphoma), inoculated subcutaneously into the AKR inbred mice. K36 lymphoma is a transformed cell line which originated from the AKR mice infected with murine leukemic retrovirus. The K36 lymphoma cells are naturally tumorigenic in syngenic AKR mice and is non-immunogenic to the host mice. The in vivo tests were carried out according to the following protocol:

Day 0: K36 lymphoma cells were washed with phosphate-buffered saline (PBS) for three times and suspended in RPMI 1640 medium at the concentration of 10×10$^6$ cells/mL 10$^6$ cells in 0.1 mL of the medium were implanted subcutaneously into each of the two flanks of inbred AKR mice with a ½-in, 28-gauge, 1-mL syringe. The mice were then randomly distributed into control and treatment groups with 5 mice/group.

Day 1–7: The desired dose of a test agent was dissolved in a minimum amount (<50 $\mu$L) of dimethylacetamide (DMA), followed by addition of Cremaphor_EL (polyethoxylated castor oil, <30 $\mu$L) with mixing. Saline was added to dilute the drug solution and the desired dose was delivered in a volume of 5×0.3 mL for one group of mice (5 mice per group). In this case, the final concentration of dimethylacetamide was less than 3.3% and that of the carrier less than 2%. Formulation of a test agent was carried out just before injection into the animals. The test agent was injected intraperitoneally into the treatment groups of mice twice a day following the flexible schedule as recommended in the literature (Corbett, T. H.; Valeriote, F. A; LoRusso, P.; Polin, L; et. al. In "Anticancer Drug Development Guide: Preclinical Screening, Clinical Trials, and Approval", (Ed. Teicher, B. A.), Humana Press Inc., Totowa, N.J., 1997 p 75–99.) to reach the most tolerated drug dose.

Day 8–11: Tumor weights were estimated from two-dimensional measurement, following the formula:

$$\text{Tumor weight (in mg)} = (a \times b^2)/2,$$

wherein a and b are tumor length and width (in mm), respectively. The usual T/C value was used to assess the in vivo anti-tumor activity. T refers to the total tumor weight of the treatment group (including zeros), whereas, C refers to the total tumor weight of the non-treatment control group (including zeros). According to the NCI (National Cancer Institute in USA) standard, a T/C value of 42% is considered significant anti-tumor activity. A T/C value <10% is an indication of a highly active agent.

Furthermore, two compounds cisplatin (cis-diaminedichloroplatinum(II)) and [Au(dppe)$_2$]Cl (dppe: 1,2-bis(diphenylphosphino)ethane) with known anti-tumor activities were also included in the In vivo test Table 2 summarizes the anti-tumor activities of $(S_p)$-1 and $(R_p)$-1.

TABLE 2

| Complexes | MTTD ($\mu$mol/kg) | MTTD* (mg/kg) | T/C** (%) |
| --- | --- | --- | --- |
| $(S_p)$-I | 55 | 52 | 5 |
| $(R_p)$-I | 55 | 52 | 6 |
| Cisplatin | 30 | 9 | 6 |
| [Au(dppe)$_2$]Cl | 10 | 10 | 12 |

*MTTD: Most Tolerated Total Dose
**T/C: (the average tumor weight of treated group/the average tumor weight of control group) × 100

Based on the data, the preferred compounds displayed high anti-tumor activities against this murine lymphoma model. Compared to the two positive controls, they are as active as cisplatin and more active than [Au(dppe)₂]Cl. As for the most active agents (e.g. ($S_p/R_p$)-I and Cisplatin), there were always a number of long-term survived mice after one course of chemotherapy, and most of them were actually cured from the cancer. For the K36 lymphoma model, a long-term survivor is defined as a mouse that survives for more than 50 days from the date of tumor implantation (the median life span for the AKR mice in the non-treatment control groups was around 20 days after the tumor implantation). A mouse that survives for more than 70 days without palpable tumor mass can be considered cured from the disease. The long-term survival ratio in those three groups usually ranged 20–40%. Moreover, the cure from the cancer is only caused by the drug itself and not aided by the immune system of the host because of the inbred AKR mice used and the nature of the K36 lymphoma.

In addition, three dose levels of 0.67 decrements were used in the secondary in vivo evaluation studies of ($S_p$)-1 and ($R_p$)-1 against the K36 lymphoma. The purpose of testing at multiple dosage levels is to exclude agents with exceptionally steep dose-response curves, where only the most tolerated dose is active. In clinical trials, an agent rarely reaches the dose that is similar to the most tolerated dose in a healthy young mouse such that a clinically useful agent should possess in vivo anti-tumor activity at least at two non-toxic dosage levels (0.67 decrements). ($S_p/R_p$)-I were selected to rechallenge the K36 tumor model at three dosage levels with 0.67 decrements: at 54, 36, and 24 µmol/kg in the secondary evaluation. The results are listed in Table 3.

TABLE 3

| Compound | Dosage (µmol/kg) | T/C (%) |
|---|---|---|
| ($S_p$)-I | 54 | 5 |
|  | 36 | 12 |
|  | 24 | 33 |
| ($R_p$)-I | 54 | 6 |
|  | 36 | 14 |
|  | 24 | 38 |

In this multi-dosage test, both ($S_p$)-I and ($R_p$)-I were still highly active in vivo against the murine K36 lymphoma at the two dose levels of 54 and 36 µmol/kg, and some mice were actually cured from the cancer after one course of chemotherapy. However, at the dosage level of 24 µmol/kg, they showed moderate activity.

The anti-tumor activities of ($S_p$)- and ($R_p$)-I were also assessed against advanced K36 lymphoma model. Also, the active positive control, cisplatin, was included in the evaluation.

The protocol design for this test was similar as described above except that drug administrations began on Day 7 (Day 0 is the date of implantation). At this stage, the tumor sizes on mice averaged around 9×8 mm and the estimated average tumor weight was about 300 mg. Due to the extremely fast growth of the K36 lymphoma (the double time is around 1 day), there was limited time (up to 4 days) to escalate the drug dosage to the most tolerated level, before the tumor became too big to give a positive response to any drug treatment. In this experiment, the MTTD for ($S_p$) and ($R_p$)-I reached 32 µmol/kg, being significantly lower than that in the primary screen in which the drug treatment lasted for 7 days. In contrast, the dosage of cisplatin was increased to 28 µmol/kg in this test with the comparable MTTD value as in the primary screen.

The results are visualised in FIG. 1. It is obvious that both ($S_p$)- and ($R_p$)-I displayed significant anti-tumor activities against the advanced K36 tumor model. They can markedly retard the tumor growth during the period of drug treatment and even after treatment. The average ILS % (Increased Life Span) of (Sp)-I and (Rp)-I was 48% and 31%, respectively (the average life span of the control group was 21 days after tumour implantation). Particularly, one mouse treated with (Sp)-I survived for 48 days after tumour implantation. However, although cisplatin was highly active in the primary screen, it did not inhibit the growth of the advanced K36 lymphoma at all.

One aspect of the invention relates to pharmaceutical compositions including compounds according to the invention and a pharmaceutically acceptable diluent or carrier, examples of which are well known in the art. The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above pharmaceutical compositions may be prepared in a conventional manner using conventional excipients.

The anti-tumor agent win normally be administered to a warm-blooded animal at a unit dose within the range 50–10000 mg per square meter body area of the animal, i.e. approximately 1–200 mg/kg, and this normally provides a therapeutically effective amount. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

We have found that the compounds of the present invention possess anti-poliferative properties (inhibition of cell growth) such as anti-tumor properties. According to a further aspect of the present invention, an effective amount of a compound according to the invention may be administered to produce an antiproliterative effect and to treat the cancer.

As stated above the size of the dose required for the therapeutic or prophylactic treatment of a particular proliferative disease will necessarily be varied depending on the host treated, the route of administration and the severity of the illness being treated. A unit dose in the range, for example, 1–200 mg/kg, preferably 1–100 mg/kg, more preferably 1–10 mg/kg is envisaged in addition to 1–50 mg/kg.

The anti-tumor effect of the compounds of the present invention may be applied as a sole therapy or may involve, in addition, one or more other substances and/or treatments.

Accordingly, in a further preferred aspect of the present invention, the process may further include administering a compound according to the invention cojointly in a unit dosage in the range of from approximately 1 to 200 mg/kg.

Such conjoint treatment may be achieved by way of simultaneous, sequential or separate administration of the individual components of the treatment. In the field of medical oncology it is normal practice to use a combination of different forms of treatment to treat each patient with cancer such as a combination of surgery, radiotherapy and/or chemotherapy. In particular, it is known that irradiation or treatment with antiangiogenic and/or vascular permeability reducing agents can enhance the amount of hypoxic tissue within a tumor. Therefore the effectiveness of the compounds of the present invention is expected to be improved by conjoint treatment with radiotherapy and/or with an antiangiogenic agent.

In general such chemotherapy may cover three main categories of therapeutic agent:

(i) antiangiogenic agents including those believed to act by way of inhibition of vascular endothelial growth factor 9VEGF, and antiangiogenic agents that work by different mechanisms, for example linomide, inhibitors of integrin αvβ3 function, angiostatin, razoxin and thalidomide;

(ii) cytostatic agents such as antioestrogens (for example tamoxifen, toremifene, raloxifene, droloxifene and iodoxyfene), progestogens (for example megestrol acetate), aromatase inhibitors (for example anastrozole, letrazole, vorazole and exemestane), antiprogestogens, antiandrogens (for example flutamide, nilutamide, bicalutamide and cyproterone acetate), LHRH agonists and antagonists (for example goserelin acetate, luprolide and buserelin), inhibitors of testosterone 5α-dihydroreductase (for example finasteride), anti-invasion agents (for example metalloprot inase inhibitors like marimastat and inhibitors of urokinase plasminogen activator receptor function) and inhibitors of growth factors (for example inhibitors of epidermal growth factor (EGF), fibroblast growth factor (FGF), platelet derived growth factor and hepatocyte growth factor such as EGF receptor tyrosine kinase inhibitors and serine/threonine kinase inhibitors); and (iii) antiproliferative, antineoplastic drugs and combinations thereof, as used in medical oncology, such as antimetabolites (for example antifolates like methotrexate and raltitrexed, fluoropyrimidines like 5-fluorouracil, purine and adenosine analogues and sytosine arabinoside); antitumor antibiotics (for example the bleomycins and anthracyclines like doxorubicin, daunomycin, epirubicin and idarubicin, mitomycin-C, dactinomycin and mithramycin); platinum derivatives (for example cisplatin and carboplatin); alkylating agents (for example nitrogen mustard, melphalan, chlorambucil, busulphan, cyclophosphamide, ifosfamide, nitrosoureas and thiotepa); antimitotic agents (for example vinca alkaloids like vincrisitine and taxoids like taxol and taxotere); topoisomerase inhibitors (for example epipodophyllotoxins like etoposide and teniposide, amsacrine and topotecan).

The pharmaceutical composition of the present invention may include an effective tumor cell growth-inhibiting amount of a compound of formula I, a diluent, or an inert pharmaceutically acceptable carrier, and may be in the form of a solution of the active component in a minimal volume of dimethylacetamide (1–3%, v/v) and a minimal volume of Cremaphor-EL (1–2%, v/v), diluted up to the volume for administration with normal saline solution.

In addition, it is noteworthy that the actual optimal dosages of the compounds of formula I in the composition for administration will vary according to the particular compound being used, the treatment duration, and host being treated. The route of internal administration should be selected to ensure than an effective tumor cell growth-inhibiting amount of the active component crosses the physiological barriers of the host and thereby contacts the tumor. The flexible drug administration schedule should be adopted to minimize toxicity to the host, as recommended in the literature (Corbett, T. H.; Val riote, F. A.; LoRusso, P.; Polin, L; et. al. in "Anticancer Drug Development Guide: preclinical Screening, Clinical Trials, and Approval", (Ed. Telcher, B. A.), Humana Press Inc., Totowa, N.J., 1997, p 75–99.)

EXAMPLES

The following examples which illustrate the chemical preparation of compounds of formula (I) are not to be construed as limiting the scope thereof. All temperatures are in degrees Centigrade.

Example 1

(1α,4α,5α(R),6β(S),7R)-5-(diphenylphosphino)-2,3-dimethyl-6-(ethoxycarbonyl)-7-phenyl-7-phosphabicyclo[2.2.1]hept-2-ene The above ligand was prepared in accordance with the method published in Inorganic Chemistry, 1988, Vol. 37, page 63–99. A mixture of ethyl propionate (0.98 g, 10 mmol), diphenylphosphine (1.86 g, 10 mmol) and glacial acetic acid (0.6 g, 10 mmol) in dichloromethane was stirred at room temperature for 2 days. The solvent was removed under reduced pressure to give a black residue. This material was chromatographed on a silica gel column (50 g, 40–63 mm) with dichloromethane-hexane (1:1 v/v) as the eluent, giving the tertiary phosphine (diphenyl[(E)-2-(ethoxycarbonyl)vinyl]phosphine) as air-sensitive colourless oil: 1.40 g (50% yield). $^{31}$P NMR (CDCl$_3$): δ −10.9.

The starting material perchlorato (R)-1-[1-(dimethylamino)ethyl]-2-naphthalenyl-C,N][3,4-dimethyl-1-phenyl-phosphole-P]palladium (II) (0.63 g, 1.06 mmol) in dichloromethane (30 mL) was treated with the tertiary phosphine (ethyl carboxylate substituted phospine) generated above (0.30 g, 1.06 mmol) at room temperature for 2 h. The solution was then concentrated to ca. 10 mL. Upon slow addition of diethyl ether to the concentrated solution, the desired palladium complex, {(R)-1-[1-(dimethylamino)ethyl]naphthyl-C2,N}{(1α,4α,5α(R),6β(S),7S)-[5-(diphenyl-phosphino)-2,3-dimethyl-6-(ethoxycarbonyl)-7-phenyl-7-phosphabicyclo[2.2.1]hept-2-ene-P5,P7}palladium (II) perchlorate was obtained as colourless prisms: 0.84G (90% YIELD), $^{31}$P NMR (CDCl$_3$): δ 53.2 (d, 1P, $^2J_{PP}$=41.5 Hz, P$^5$),[α]$_D$ −4.4 (c 0.5, CH$_2$Cl$_2$).

The naphthylamine auxiliary was removed chemoselectively by dissolving the above complex (0.5 g, 0.57 mmol) in concentrated sulfuric acid (30 mL, 70%). Addition of the acidic solution to crushed ice (100 g) followed by treatment with lithium chloride (0.51 g, 12.0 mmol) gave the dichloro complex ([SP-4-2-(1α,4α,5α(R),6β(S),7R)]-dichloro{5-(diphenylphosphino)-2,3-dimethyl-6-(ethoxycarbonyl)-7-phenyl-7-phospha-bicyclo[2.2.1]hept-2-ene-P5,P7}palladium (II)) as a white precipitate. The crude complex was subsequently filtered off, washed with water (3×10 mL) and ethanol (3×10 mL), and recrystallised from dichloromethane-diethyl ether as pale yellow blocks:

0.35 g (94% yield), $^{31}$P NMR (CDCl$_3$): δ 35.2 (d, 1P, $^2J_{PP}$=4.0 Hz, P$^5$), 133.4 (d, 1P, $^2J_{PP}$=4.0 Hz, P$^7$) [α]$_D$ +76.7 (c 0.5, CH$_2$Cl$_2$), mp 272–275° C. Liberation of the desired diphosphine from the dichloro complex was achieved by treating a dichloromethane (20 mL) solution of the dichloro complex (0.32 g, 0.5 mmol) with potassium cyanide (2.5 g, 40 mmol) in water (10 mL) at room temperature for 15 min. The organic layer was separated from the mixture, washed with water (3×10 mL) and dried over MgSO$_4$. Upon removal of the solvent, the diphosphine ((1α,4α,5α(R),6β(S),7R)-5-(diphenylphosphino)-2,3-dimethyl-6-(ethoxy-carbonyl)-7- phenyl-7-phosphabicyclo[2.2.1]hept-2-ene) was obtained as an air-sensitive colourless oil: 0.20 g (86% yield), $^{31}$P NMR (CDCl$_3$): δ −4.4 (d, 1P, $^2J_{PP}$=70.5 Hz, P$^5$), 103.8 (d, 1P, $^2J_{PP}$=70.5 Hz, P$^7$), [α]$_D$=+204.5 (c 0.5, CH$_2$Cl$_2$).

Example 2

μ-{(1α,4α,5α(R),6β(S),7S)-5-(Diphenylphosphino)-2,3-dimethyl-6-(ethoxycarbonyl)-7-phenyl-7-phosphabicyclo[2.2.1]hept-2-ene-P5,P7}bis[chlorogold(I)] ie (S$_p$)-I To a solution of (1α,4α,5α(R),6β(S),7R)-5-(diphenylphosphino)-2,3-dimethyl-6-(ethoxycarbonyl)-7-phenyl-7-phosphabicyclo[2.2.1]hept-2-ene (Example 1) (0.24 g, 0.5 mmol) in dichloromethane (15 mL) was added a solution of chloro(dimethyl sulfide)gold(I) (0.29 g, 1 mmol) in the same solvent (15 mL). The reaction mixture was allowed to stir in darkness for three hours (at room temperature of about 30° C.). Upon removal of the resulting dimethyl sulfide and the solvent under reduced pressure at room temperature, the residue was crystallized from dichloromethane and diethyl ether to obtain (Sp)-1 as colorless prisms: yield 0.25 g (54%); m.p. 227–229° C. (dec.); [α]$_D$=+77° (c=0.7, CH$_2$Cl$_2$); $^{31}$P NMR (CDCl$_3$): δ 42.2 (d, 1P, J$_{PP}$=13.4 Hz, P$^5$), 100.8 (d, 1P, J$_{PP}$=13.4 Hz, P$^7$); $^1$H NMR (CDCl$_3$): δ 1.21 (t, 3H, $^3J_{HH}$=7 Hz, OCH$_2$Me), 1.25 (s, 3H, C=CMe), 1.68 (s, 3H, C=CMe), 3.4–3.7 (m, 4H, alicylics), 4.03 (q, 2H, $^3J_{HH}$=7 Hz, OCH$_2$Me), 7.2–8.2 (m, 15H, aromatics). Anal. Calcd for C$_{29}$H$_{30}$Au$_2$Cl$_2$O$_2$P$_2$H$_2$O: C, 36.5, H, 3.4; Found C, 36.5, H, 3.4.

Example 3

μ{(1α,4α,5α(S),6β(R),7R)-5-(Diphenylphosphino)-2,3-dimethyl-6-(ethoxy-carbonyl)-7-phenyl-7-phosphabicyclo[2.2.1]hept-2-ene-P5,P7}bis[chlorogold(I)] ie (R$_p$)-I To a solution of (1α,4α,5α(S),6β(R),7S)-5-(diphenylphosphino)-2,3-dimethyl-6-(ethoxy-carbonyl)-7-phenyl-7-phosphabicyclo[2.2.1]hept-2-ene (the enantiomer of Example 1 which may be obtained by using the other hand form as the starting material i.e. perchlorato (S)-1-[1-(dimethylamino)ethyl]-2-naphthalenyl-C,N][3,4-dimethyl-1-phenyl-phosphole-P]palladium (II)) (0.24 g, 0.5 mmol) in dichloromethane (15 mL) was added a solution of chloro (dimethyl sulfide)gold(I) (0.29 g, 1 mmol) in the same solvent (15 mL). The reaction mixture was allowed to stir in darkness for three hours (at room temperature of about 30° C). Upon removal of the resulting dimethyl sulfide and the solvent under reduced pressure at room temperature, the residue was crystallized from dichloromethane and diethyl ether to obtain the product (Rp)-1 as colorless prisms: yield 0.25 g (54%); m.p. 227–229° C. (dec.); [α]$_D$=−77° (c=0.7, CH$_2$Cl$_2$); $^{31}$P NMR (CDCl$_3$): δ 42.2 (d, 1P, J$_{PP}$=13.4 Hz, P$^5$), 100.8 (d, 1P, J$_{PP}$=13.4 Hz, P$^7$); $^1$H NMR (CDCl$_3$): δ 1.21 (t, 3H, $^3J_{HH}$=7 Hz, OCH$_2$Me), 1.25 (s, 3H, C=CMe), 1.68 (s, 3H, C=CMe), 3.4–3.7 (m, 4H, alicylics), 4.03 (q, 2H, $^3J_{HH}$=7 Hz, OCH$_2$Me), 7.2–8.2 (m, 15H, aromatics).

Finally, it is to be understood that various alterations, modifications and/or additions may be made without departing from the spirit of the present invention as outlined herein.

What is claimed is:

1. A phosphino-gold(I) compound of formula (I):

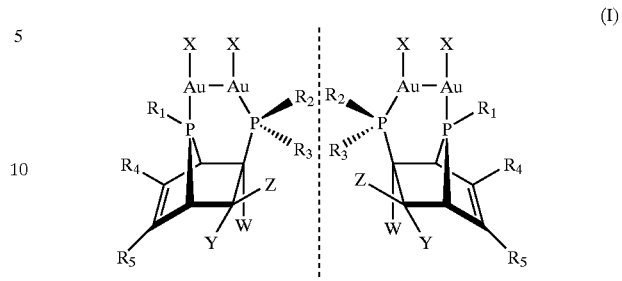

wherein R$_1$, R$_2$, R$_3$, R$_4$ and R$_5$, each of which may be the same or different, are selected from the group consisting of hydrogen, optionally substituted alkyl, aryl, alkenyl, alkynyl, hydroxyalkyl, alkoxy, aryloxy, carboxyalkyl, alkoxycarbonyl, hydroxy, alkylthio, alkylsulfinyl and alkylsulfonyl;

Z is hydrogen or a functional group;

Y is hydrogen or a functional group;

W is hydrogen or a functional group; and

X is a halogen or C(F)$_3$ or C(Cl)$_3$ in an optically active or racemic form; or salt thereof.

2. A phosphino-gold(I) compound according to claim 1 wherein the functional group for each of Z, Y and W is hydroalkyl, alkoxy, aryloxy, carboxyalkyl, alkoxycarbonyl, hydroxy, alkylthio, alkylsulfinyl or alkylsulfonyl.

3. A phosphino-gold(I) compound according to claim 2 wherein alkyl groups contain up to 10 carbon atoms.

4. A phosphino-gold(I) compound according to claim 3, wherein each of R$_1$, R$_2$, R$_3$, R$_4$, and R$_5$ is independently hydrogen or an optionally substituted alkyl or aryl group.

5. A phosphino-gold(I) compound according to claim 4 wherein each of R$_1$, R$_2$, and R$_3$, is independently an aryl group, and each of R$_4$ and R$_5$ is independently methyl.

6. A phosphino-gold(I) compound according to claim 4, wherein each of R$_1$, R$_2$ and R$_3$ is independently an optionally substituted phenyl group.

7. A phosphino-gold(I) compound according to claim 6 wherein the phenyl group is substituted with (1–4C) alkoxy.

8. A phosphino-gold(I) compound according to claim 7 wherein the alkoxy is methoxy.

9. A phosphino-gold(I) compound according to claim 6, wherein each of R$_4$ and R$_5$ is independently hydrogen, methyl, ethyl, propyl or butyl.

10. A phosphino-gold(I) compound according to claim 9, wherein Z and W are hydrogen and Y is an ethoxycarbonyl.

11. A phosphino-gold(I) compound according to claim 1, wherein R$_1$, R$_2$ and R$_3$ are phenyl, R$_4$ and R$_5$ are methyl, X is chloro, Y is ethoxycarbonyl, Z and W are hydrogen.

12. An optically active isomer of a phosphino-gold(I) compound according to claim 1.

13. The phosphino-gold(I) compound according to claim 11, which is an S$_p$ enantiomer.

14. The phosphino-gold(I) complex according to claim 11, which is an R$_p$ enantiomer.

15. A phosphino-gold(I) compound of formula (II)

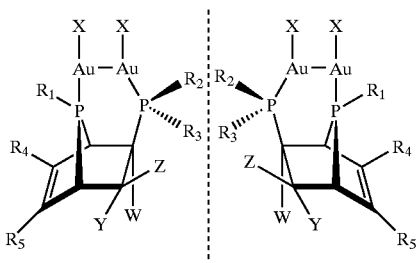

wherein
R$_1$=aryl or alkyl
R$_2$=aryl or alkyl
R$_3$=aryl or alkyl
R$_4$=aryl or alkyl
R$_5$=aryl or alkyl
Z=H or functional group
Y=H or functional group
W=H or functional group
X=halogen or C(F$_3$) or C(Cl)$_3$
in an optically active or racemic form;
or a salt thereof.

16. A phosphino-gold(I) compound according to claim 15 wherein the functional group is hydroalkyl, alkoxy, aryloxy, carboxyalkyl, alkoxycarbonyl, hydroxy, alkylthio, alkylsulfinyl or alkylsulfonyl.

17. A phospino-gold(I) compound according to claim 16 wherein alkyl groups contain up to 10 carbon atoms.

18. A phosphino-gold(I) compound according to claim 17, wherein R$_1$, R$_2$ and R$_3$ are phenyl, R$_4$ and R$_5$ are methyl, Z and W are hydrogen and Y is ethoxycarbonyl.

19. A phospino-gold(I) compound according to claim 1, selected from

μ-{(1α,4α,5α(R),6β(S),7S)-5-(Diphenylphosphino)-2,3-dimethyl-6-(ethoxy-carbonyl)-7-phenyl-7-phosphabicyclo[2.2.1]hept-2-ene-P5,P7}bis[chlorogold(I)] ("(S$_p$)-I")

μ-{(1α,4α,5α(S),6β(R),7R)-5-(Diphenylphosphino)-2,3-dimethyl-6-(ethoxy-carbonyl)-7-phenyl-7-phosphabicyclo[2.2.1]hept-2-ene-P5,P7}bis[chlorogold(I)] ("R$_p$)-I").

20. A process for the preparation of a phosphino-gold(I) compound of formula (I)

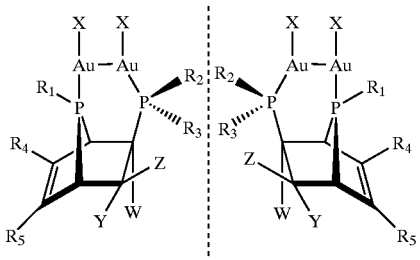

wherein R$_1$, R$_2$, R$_3$, R$_4$ and R$_5$, each of which may be the same or different, are selected from the group consisting of hydrogen, optionally substituted alkyl, aryl, alkenyl, alkynyl, hydroxyalkyl, alkoxy, aryloxy, carboxyalkyl, alkoxycarbonyl, hydroxy, alkylthio, alkylsulfinyl and alkylsulfonyl;

Z is hydrogen or a functional group;
Y is hydrogen or a functional group;
W is hydrogen or a functional group; and
X is a halogen C(F)$_3$ or C(Cl)$_3$ in an optically active or racemic form; or a salt thereof; which process comprises reacting a compound of formula (III) with a halo gold(I) compound to form a phosphino-gold(I) compound

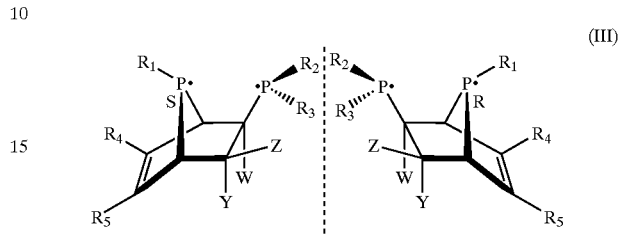

(III)

wherein R$_1$, R$_2$, R$_3$, R$_4$, and R$_5$, each of which may be the same or different, are selected from the group consisting of hydrogen, optionally substituted alkyl, aryl, alkenyl, alkynyl, hydroxyalkyl, alkoxy, aryloxy, carboxyalkyl, alkoxycarbonyl, hydroxy, alkylthio, alkylsulfinyl and alkylsulfonyl;

Z is hydrogen or a functional group;
Y is hydrogen or a functional group; and
W is hydrogen or a functional group.

21. The process according to claim 20, wherein the halogold(I) compound is a chloro(dimethy sulfide)gold(I) compound.

22. The process according to claim 21, wherein an (S$_p$)-ligand of formula (III) is reacted with the halogold compound.

23. The process according to claim 21 wherein the halogold(I) compound is reacted with (1α,4α,5α(R),6β(S),7R)-5-(diphenylphosphino)-2,3-dimethyl-6-(ethoxycarbonyl)-7-phenyl-7-phosphabicyclo[2.2.1]hept-2-ene.

24. The process according to claim 21 wherein an (R$_p$)-ligand of formula (III) is reacted with the halogold compound.

25. The process according to claim 21 wherein the halogold (I) compound is reacted with (1α,4α,5α(S),6β(R)-7S)-5-(diphenylphosphino)-2,3-dimethyl-6-(ethoxy-carbonyl)-7-phenyl-7-phosphabicyclo[2.2.1]hept-2-ene.

26. The process according to claim 20 wherein the compounds are reacted in a non-reactive organic solvent for a time sufficient and at a temperature sufficient to permit the compounds to fully react.

27. The process according to claim 26, wherein the compounds are reacted in a solution of dichloromethane at ambient temperatures for a period of approximately 1 to 5 hours.

28. The process according to claim 27 wherein the compounds are reacted for 3 hours at about 30° C.

29. A pharmaceutical composition comprising an effective amount of a phosphino-gold(I) compound of formula (I) as claimed in claim 1 in an optically active or racemic form, or a pharmaceutically acceptable salt thereof and a pharmaceutically acceptable diluent or carrier.

30. The pharmaceutical composition according to claim 29 wherein the compound is μ-{(1α,4α,5α(R),6β(S),7S)-5-(Diphenylphosphino)-2,3-dimethyl-6-(ethoxy-carbonyl)-7-phenyl-7-phosphabicyclo[2.2.1]hept-2-ene-P5,P7}bis[chlorogold(I)] ("(S$_p$)-I") or μ-{(1α,4α,5α(S),6β(R),7R)-5-

(Diphenylphosphino)-2,3-dimethyl-6-(ethoxy-carbonyl)-7-phenyl-7-phosphabicyclo[2.2.1]hept-2-ene-P5,P7}bis[chlorogold(I)] ("($R_p$)-I").

31. The pharmaceutical composition according to claim 29 wherein the compound is according to claim 15.

32. The pharmaceutical composition according to claim 30 in a unit dosage form.

33. A process for producing an anti-proliferative effect in a warm-blooded animal in need of such treatment comprising
administering to said animal an effective amount of a compound of a phosphino-gold(I) compound of formula (I) as claimed in claim 1 in an optically active or racemic form, or a pharmaceutically-acceptable salt thereof.

34. The process according to claim 33 wherein the compound is $\mu$-{(1α,4α,5α(R),6β(S),7S)-5-(Diphenylphosphino)-2,3-dimethyl-6-(ethoxy-carbonyl)-7-phenyl-7-phosphabicyclo[2.2.1]hept-2-ene-P5,P7}bis[chlorogold(I)] ("($S_p$)-I") or $\mu$-{(1α,4α,5α(S),6β(R),7R)-5-(Diphenylphosphino)-2,3-dimethyl-6-(ethoxy-carbonyl)-7-phenyl-7-phosphabicyclo[2.2.1]hept-2-ene-P5,P7}bis[chlorogold(I)] ("($R_p$)-I").

35. The process according to claim 34, wherein the compound is administered in a unit dosage in the range of from approximately 1 to 200 mg/kg.

36. A process for treating cancer of a patient comprising administering to said patient an effective amount of a phosphino-gold(I) compound of formula (I) as claimed in claim 1 in an optically active or racemic form, or a pharmaceutically-acceptable salt thereof.

37. The process according to claim 36 wherein the cancer is tumorous.

38. The process according to claim 37 wherein the phospino-gold(I) compound is $\mu$-{(1α,4α,5α(R),6β(S),7S)-5-(Diphenylphosphino)-2,3-dimethyl-6-(ethoxy-carbonyl)-7-phenyl-7-phoshabicyclo[2.2.1]hept-2-ene-P5,P7}bis[chlorogold(I)] ("($S_p$)-I") or $\mu$-{(1α,4α,5α(S),6β(R),7R)-5-(Diphenylphosphino)-2,3-dimethyl-6-(ethoxy-carbonyl)-7-phenyl-7-phosphabicyclo[2.2.1]hept-2-ene-P5,P7}bis[chlorogold(I)] ("($R_p$)-I").

39. The process according to claim 38, wherein the compound is administered in a unit dosage in the range of from approximately 1 to 200 mg/kg.

40. The process according to claim 39, wherein the compound is administered conjointly with radiotherapy and/or with the administration of a therapeutic agent selected from the group consisting of anti-angiogenic agents, cytostatic agents, and anti-proliferafive anti-neoplastic agents, and combinations thereof.

41. The process according to claim 33 wherein the phosphino-gold(I) compound is according to claim 15.

42. The process according to claim 37 wherein the phosphino-gold(I) compound is according to claim 15.

43. A phosphino-gold(I) compound according to claim 7, wherein each of $R_4$ and $R_5$ is independently hydrogen, methyl, ethyl, propyl or butyl.

44. A phosphino-gold(I) compound according to claim 8, wherein each of $R_4$ and $R_5$ is independently hydrogen, methyl, ethyl, propyl or butyl.

45. An optically active isomer of a phosphino-gold(I) compound according to claim 2.

46. An optically active isomer of a phosphino-gold(I) compound according to claim 3.

47. An optically active isomer of a phosphino-gold(I) compound according to claim 4.

48. An optically active isomer of a phosphino-gold(I) compound according to claim 5.

49. An optically active isomer of a phosphino-gold(I) compound according to claim 6.

50. An optically active isomer of a phosphino-gold(I) compound according to claim 7.

51. An optically active isomer of a phosphino-gold(I) compound according to claim 8.

52. An optically active isomer of a phosphino-gold(I) compound according to claim 9.

53. An optically active isomer of a phosphino-gold(I) compound according to claim 43.

54. An optically active isomer of a phosphino-gold(I) compound according to claim 44.

55. An optically active isomer of a phosphino-gold(I) compound according to claim 10.

56. An optically active isomer of a phosphino-gold(I) compound according to claim 11.

57. The process according to claim 21 wherein the compounds are reacted in a non-reactive organic solvent for a time sufficient and at a temperature sufficient to permit the compounds to fully react.

58. The process according to claim 22 wherein the compounds are reacted in a non-reactive organic solvent for a time sufficient and at a temperature sufficient to permit the compounds to fully react.

59. The process according to claim 23 wherein the compounds are reacted in a non-reactive organic solvent for a time sufficient and at a temperature sufficient to permit the compounds to fully react.

60. The process according to claim 24 wherein the compounds are reacted in a non-reactive organic solvent for a time sufficient and at a temperature sufficient to permit the compounds to fully react.

61. The process according to claim 25 wherein the compounds are reacted in a non-reactive organic solvent for a time sufficient and at a temperature sufficient to permit the compounds to fully react.

62. The pharmaceutical composition according to claim 29 wherein the compound is according to claim 2.

63. The pharmaceutical composition according to claim 29 wherein the compound is according to claim 3.

64. The pharmaceutical composition according to claim 29 wherein the compound is according to claim 4.

65. The pharmaceutical composition according to claim 29 wherein the compound is according to claim 5.

66. The pharmaceutical composition according to claim 29 wherein the compound is according to claim 6.

67. The pharmaceutical composition according to claim 29 wherein the compound is according to claim 7.

68. The pharmaceutical composition according to claim 29 wherein the compound is according to claim 8.

69. The pharmaceutical composition according to claim 29 wherein the compound is according to claim 9.

70. The pharmaceutical composition according to claim 29 wherein the compound is according to claim 43.

71. The pharmaceutical composition according to claim 29 wherein the compound is according to claim 44.

72. The pharmaceutical composition according to claim 29 wherein the compound is according to claim 10.

73. The pharmaceutical composition according to claim 29 wherein the compound is according to claim 11.

74. The pharmaceutical composition according to claim 29 wherein the compound is according to claim 12.

75. The pharmaceutical composition according to claim 29 wherein the compound is according to claim 45.

76. The pharmaceutical composition according to claim 29 wherein the compound is according to claim 46.

77. The pharmaceutical composition according to claim 29 wherein the compound is according to claim 47.

78. The pharmaceutical composition according to claim 29 wherein the compound is according to claim 48.
79. The pharmaceutical composition according to claim 29 wherein the compound is according to claim 49.
80. The pharmaceutical composition according to claim 29 wherein the compound is according to claim 50.
81. The pharmaceutical composition according to claim 29 wherein the compound is according to claim 51.
82. The pharmaceutical composition according to claim 29 wherein the compound is according to claim 52.
83. The pharmaceutical composition according to claim 29 wherein the compound is according to claim 53.
84. The pharmaceutical composition according to claim 29 wherein the compound is according to claim 54.
85. The pharmaceutical composition according to claim 29 wherein the compound is according to claim 55.
86. The pharmaceutical composition according to claim 29 wherein the compound is according to claim 56.
87. The pharmaceutical composition according to claim 29 wherein the compound is according to claim 13.
88. The pharmaceutical composition according to claim 29 wherein the compound is according to claim 14.
89. The pharmaceutical composition according to claim 29 wherein the compound is according to claim 16.
90. The pharmaceutical composition according to claim 29 wherein the compound is according to claim 17.
91. The pharmaceutical composition according to claim 29 wherein the compound is according to claim 18.
92. The process according to claim 33 wherein the phosphino-gold(I) compound is according to claim 2.
93. The process according to claim 33 wherein the phosphino-gold(I) compound is according to claim 3.
94. The process according to claim 33 wherein the phosphino-gold(I) compound is according to claim 4.
95. The process according to claim 33 wherein the phosphino-gold(I) compound is according to claim 5.
96. The process according to claim 33 wherein the phosphino-gold(I) compound is according to claim 6.
97. The process according to claim 33 wherein the phosphino-gold(I) compound is according to claim 7.
98. The process according to claim 33 wherein the phosphino-gold(I) compound is according to claim 8.
99. The process according to claim 33 wherein the phosphino-gold(I) compound is according to claim 9.
100. The process according to claim 33 wherein the phosphino-gold(I) compound is according to claim 43.
101. The process according to claim 33 wherein the phosphino-gold(I) compound is according to claim 44.
102. The process according to claim 33 wherein the phosphino-gold(I) compound is according to claim 10.
103. The process according to claim 33 wherein the phosphino-gold(I) compound is according to claim 11.
104. The process according to claim 33 wherein the phosphino-gold(I) compound is according to claim 12.
105. The process according to claim 33 wherein the phosphino-gold(I) compound is according to claim 45.
106. The process according to claim 33 wherein the phosphino-gold(I) compound is according to claim 46.
107. The process according to claim 33 wherein the phosphino-gold(I) compound is according to claim 47.
108. The process according to claim 33 wherein the phosphino-gold(I) compound is according to claim 48.
109. The process according to claim 33 wherein the phosphino-gold(I) compound is according to claim 49.
110. The process according to claim 33 wherein the phosphino-gold(I) compound is according to claim 50.
111. The process according to claim 33 wherein the phosphino-gold(I) compound is according to claim 51.
112. The process according to claim 33 wherein the phosphino-gold(I) compound is according to claim 52.
113. The process according to claim 33 wherein the phosphino-gold(I) compound is according to claim 53.
114. The process according to claim 33 wherein the phosphino-gold(I) compound is according to claim 54.
115. The process according to claim 33 wherein the phosphino-gold(I) compound is according to claim 55.
116. The process according to claim 33 wherein the phosphino-gold(I) compound is according to claim 56.
117. The process according to claim 33 wherein the phosphino-gold(I) compound is according to claim 13.
118. The process according to claim 33 wherein the phosphino-gold(I) compound is according to claim 14.
119. The process according to claim 33 wherein the phosphino-gold(I) compound is according to claim 16.
120. The process according to claim 33 wherein the phosphino-gold(I) compound is according to claim 17.
121. The process according to claim 33 wherein the phosphino-gold(I) compound is according to claim 18.
122. The process according to claim 37 wherein the phosphino-gold(I) compound is according to claim 2.
123. The process according to claim 37 wherein the phosphino-gold(I) compound is according to claim 3.
124. The process according to claim 37 wherein the phosphino-gold(I) compound is according to claim 4.
125. The process according to claim 37 wherein the phosphino-gold(I) compound is according to claim 5.
126. The process according to claim 37 wherein the phosphino-gold(I) compound is according to claim 6.
127. The process according to claim 37 wherein the phosphino-gold(I) compound is according to claim 7.
128. The process according to claim 37 wherein the phosphino-gold(I) compound is according to claim 8.
129. The process according to claim 37 wherein the phosphino-gold(I) compound is according to claim 9.
130. The process according to claim 37 wherein the phosphino-gold(I) compound is according to claim 43.
131. The process according to claim 37 wherein the phosphino-gold(I) compound is according to claim 44.
132. The process according to claim 37 wherein the phosphino-gold(I) compound is according to claim 10.
133. The process according to claim 37 wherein the phosphino-gold(I) compound is according to claim 11.
134. The process according to claim 37 wherein tho phosphino-gold(I) compound is according to claim 12.
135. The process according to claim 37 wherein the phosphino-gold(I) compound is according to claim 45.
136. The process according to claim 37 wherein the phosphino-gold(I) compound is according to claim 46.
137. The process according to claim 37 wherein the phosphino-gold(I) compound is according to claim 47.
138. The process according to claim 37 wherein the phosphino-gold(I) compound is according to claim 48.
139. The process according to claim 37 wherein the phosphino-gold(I) compound is according to claim 49.
140. The process according to claim 37 wherein the phosphino-gold(I) compound is according to claim 50.
141. The process according to claim 37 wherein the phosphino-gold(I) compound is according to claim 51.
142. The process according to claim 37 wherein the phosphino-gold(I) compound is according to claim 52.
143. The process according to claim 37 wherein the phosphino-gold(I) compound is according to claim 53.
144. The process according to claim 37 wherein the phosphino-gold(I) compound is according to claim 54.

145. The process according to claim 37 wherein the phosphino-gold(I) compound is according to claim 55.

146. The process according to claim 37 wherein the phosphino-gold(I) compound is according to claim 56.

147. The process according to claim 37 wherein the phosphino-gold(I) compound is according to claim 13.

148. The process according to claim 37 wherein the phosphino-gold(I) compound is according to claim 14.

149. The process according to claim 37 wherein the phosphino-gold(I) compound is according to claim 16.

150. The process according to claim 37 wherein the phosphino-gold(I) compound is according to claim 17.

151. The process according to claim 37 wherein the phosphino-gold(I) compound is according to claim 18.

\* \* \* \* \*